United States Patent
Sinay et al.

(10) Patent No.: US 11,559,191 B2
(45) Date of Patent: Jan. 24, 2023

(54) INSERTION UNIT FOR MEDICAL INSTRUMENTS AND AN INTUBATION SYSTEM THEREOF

(71) Applicant: G.I. View Ltd., Ramat Gan (IL)

(72) Inventors: Avraham Sinay, Petach-Tikva (IL); Yuval Raz, Modiin (IL); Zohar Deli, Ramat Bet Shemesh (IL); Ziv Rozenker, Ramat-Gan (IL); Albert Sviridovski, Petah-Tikva (IL)

(73) Assignee: G.I. VIEW LTD., Ramat Gan (IL)

( * ) Notice: Subject to any disclaimer, the term of this patent is extended or adjusted under 35 U.S.C. 154(b) by 0 days.

(21) Appl. No.: 16/455,202

(22) Filed: Jun. 27, 2019

(65) Prior Publication Data
US 2020/0129046 A1  Apr. 30, 2020

Related U.S. Application Data

(60) Provisional application No. 62/752,003, filed on Oct. 29, 2018.

(51) Int. Cl.
*A61B 1/005* (2006.01)
*A61B 1/00* (2006.01)
(Continued)

(52) U.S. Cl.
CPC ............ *A61B 1/0055* (2013.01); *A61B 1/008* (2013.01); *A61B 1/0057* (2013.01);
(Continued)

(58) Field of Classification Search
CPC . A61B 1/00071; A61B 1/00078; A61B 1/012; A61B 1/005; A61B 1/0051;
(Continued)

(56) References Cited

U.S. PATENT DOCUMENTS 3,998,216 A  12/1976 Hosono
4,432,349 A  2/1984 Oshiro
(Continued)

FOREIGN PATENT DOCUMENTS

CN  102789050 A  11/2012
CN  102469917 B  12/2014
(Continued)

OTHER PUBLICATIONS

ECRI Institute, "Top 10 Health Technology Hazards for 2011", Reprinted from vol. 39 Issue 11, Nov. 2010, 16 pages.
(Continued)

*Primary Examiner* — Ryan N Henderson
*Assistant Examiner* — Pamela F Wu
(74) *Attorney, Agent, or Firm* — Kenealy Vaidya LLP

(57) ABSTRACT

The present invention discloses an insertion unit, a bending section and an intubation system for use in a body lumen of a patient. The insertion unit comprises an inner elongated shaft structure being capable of torque transmission around its length axis and having spring-like and flexibility properties and an outer elongated shaft structure at least partially surrounding the inner elongated shaft structure and having spring-like properties and a continuous and flat outer surface. The inner elongated shaft structure has a distal end, and is capable of being connected to an optical head. The insertion unit is configured to transmit pushing and rotation forces along a length of the insertion unit. The integral insertion unit is configured and operable to bend the distal tip in all directions and to fully rotate the distal tip.

10 Claims, 9 Drawing Sheets

(51) Int. Cl.
*A61B 1/008* (2006.01)
*G02B 23/24* (2006.01)
*A61B 1/31* (2006.01)

(52) U.S. Cl.
CPC ...... *A61B 1/00071* (2013.01); *A61B 1/00147* (2013.01); *A61B 1/31* (2013.01); *G02B 23/2476* (2013.01)

(58) Field of Classification Search
CPC . A61B 1/008; A61B 1/00064; A61B 1/00073; A61B 1/00075; A61B 1/00105; A61B 1/31; A61B 1/0055–0058; A61B 1/01; A61M 2025/0004
USPC ........ 600/114, 128, 130, 136–137, 139–141, 600/121–125, 129
See application file for complete search history.

(56) References Cited

U.S. PATENT DOCUMENTS

| | | | |
|---|---|---|---|
| 4,686,963 | A | 8/1987 | Cohen et al. |
| 4,700,693 | A | 10/1987 | Lia et al. |
| 4,748,969 | A | 6/1988 | Wardle |
| 4,770,188 | A | 9/1988 | Chikama |
| 4,826,087 | A | 5/1989 | Chinery |
| 4,911,148 | A | 3/1990 | Sosnowski et al. |
| 5,005,558 | A | 4/1991 | Aomori |
| 5,137,013 | A | 8/1992 | Chiba et al. |
| 5,174,276 | A | 12/1992 | Crockard |
| 5,174,277 | A | 12/1992 | Matsumaru |
| 5,179,935 | A | 1/1993 | Miyagi |
| 5,325,845 | A | 7/1994 | Adair |
| 5,381,782 | A | 1/1995 | Delarama et al. |
| 5,520,222 | A | 5/1996 | Chikama |
| 5,601,537 | A | 2/1997 | Frassica |
| 5,679,216 | A | 10/1997 | Takayama et al. |
| 5,873,817 | A | 2/1999 | Kokish et al. |
| 5,899,914 | A | 5/1999 | Zirps et al. |
| 6,013,024 | A | 1/2000 | Mitsuda et al. |
| 6,270,453 | B1 | 8/2001 | Sakai |
| 6,364,828 | B1 | 4/2002 | Yeung et al. |
| 6,875,170 | B2 | 4/2005 | Francois et al. |
| 7,052,489 | B2 | 5/2006 | Griego et al. |
| 7,147,650 | B2 | 12/2006 | Lee |
| 7,591,783 | B2 | 9/2009 | Boulais et al. |
| 7,637,905 | B2 | 12/2009 | Saadat et al. |
| 8,182,417 | B2 * | 5/2012 | Danitz ................. A61B 1/0055 600/141 |
| 8,512,228 | B2 | 8/2013 | Vargas |
| 8,550,989 | B2 | 10/2013 | Dohi et al. |
| 9,155,451 | B2 | 10/2015 | Smith et al. |
| 2002/0017515 | A1 | 2/2002 | Obata et al. |
| 2002/0133077 | A1 | 9/2002 | Edwardsen et al. |
| 2003/0176849 | A1 | 9/2003 | Wendlandt et al. |
| 2004/0138525 | A1 | 7/2004 | Saadat et al. |
| 2004/0199052 | A1 | 10/2004 | Banik et al. |
| 2004/0242966 | A1 | 12/2004 | Barry et al. |
| 2005/0065397 | A1 | 3/2005 | Saadat et al. |
| 2006/0146127 | A1 | 7/2006 | Bagley et al. |
| 2007/0232858 | A1 | 10/2007 | Macnamara et al. |
| 2007/0276430 | A1 | 11/2007 | Lee et al. |
| 2008/0065116 | A1 | 3/2008 | Lee et al. |
| 2008/0214897 | A1 * | 9/2008 | Matsuo ................ A61B 1/0055 600/139 |
| 2009/0171159 | A1 | 7/2009 | Dennis et al. |
| 2009/0182268 | A1 | 7/2009 | Thielen et al. |
| 2009/0234186 | A1 | 9/2009 | Lin et al. |
| 2009/0240110 | A1 | 9/2009 | Miyawaki et al. |
| 2009/0299344 | A1 | 12/2009 | Lee et al. |
| 2010/0298642 | A1 | 11/2010 | Trusty et al. |
| 2010/0324370 | A1 | 12/2010 | Dohi et al. |
| 2011/0238108 | A1 | 9/2011 | Peine et al. |
| 2011/0288374 | A1 | 11/2011 | Hadani et al. |
| 2012/0029281 | A1 * | 2/2012 | Frassica ............. A61B 1/00082 600/114 |
| 2012/0029283 | A1 * | 2/2012 | Yamakawa ........ G02B 23/2476 600/114 |
| 2012/0053607 | A1 | 3/2012 | Adams |
| 2012/0238817 | A1 * | 9/2012 | Ohta .................. A61B 1/00135 600/115 |
| 2012/0277671 | A1 | 11/2012 | Fuentes |
| 2015/0066033 | A1 | 3/2015 | Jorgensen |
| 2015/0080649 | A1 | 3/2015 | Ayrenschmalz et al. |
| 2016/0296105 | A1 | 10/2016 | Ramsey |

FOREIGN PATENT DOCUMENTS

| | | |
|---|---|---|
| CN | 102596064 B | 2/2015 |
| EP | 1017323 A1 | 7/2000 |
| EP | 2248483 A4 | 3/2014 |
| EP | 3184026 A1 | 6/2017 |
| JP | 2573602 B2 | 7/1993 |
| JP | H06343702 A | 12/1994 |
| JP | 2011083549 A | 4/2011 |
| WO | 03105671 A2 | 12/2003 |
| WO | 2009107792 A1 | 9/2009 |

OTHER PUBLICATIONS

Spach, David H. et al., "Transmission of Infection by Gastrointestinal Endoscopy and Bronchoscopy", Annals of Internal Medicine vol. 118, No. 2, Jan. 15, 1993, pp. 117-128

Wayne, Jerome D. et al., "Colonoscopy: Principles and Practice", Jul. 2009, pp. 327-328

* cited by examiner

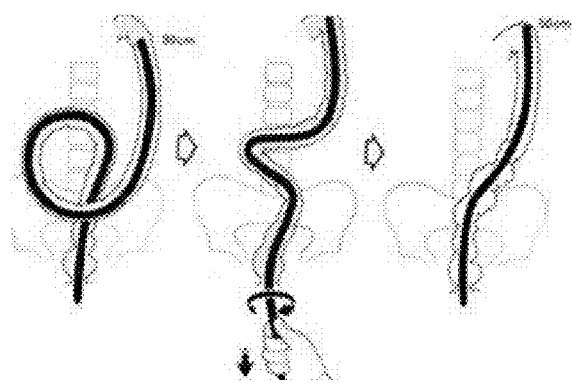
Fig. 1A GENERAL ART
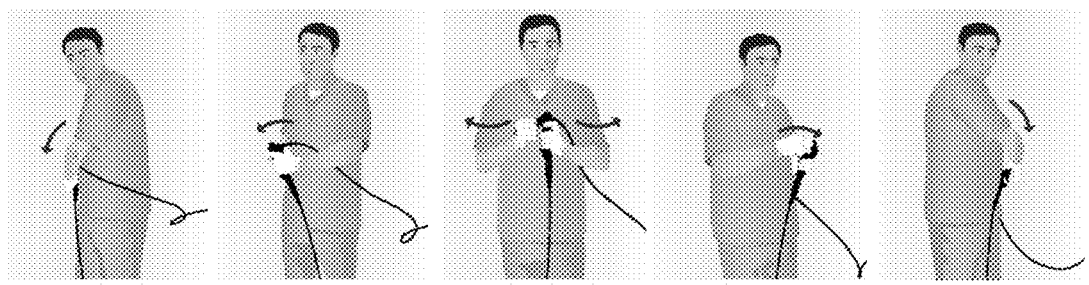
Fig. 1B     Fig. 1C     Fig. 1D     Fig. 1E     Fig. 1F
GENERAL ART

INSERTION UNIT FOR MEDICAL INSTRUMENTS AND AN INTUBATION SYSTEM THEREOF

TECHNOLOGICAL FIELD

The present invention relates generally to the field of multidirectional medical instruments, and more specifically, to steerable medical instruments.

BACKGROUND ART

References considered to be relevant as background to the presently disclosed subject matter are listed below:
U.S. Pat. No. 5,601,537;
US patent publication number 2004/0199052;
US patent publication number 2005/0065397;
US patent publication number 2009/0240110;
US patent publication number 2010/0298642;
US patent publication number 2011/0288374;
US patent publication number 2016/0296105.

Acknowledgement of the above references herein is not to be inferred as meaning that these are in any way relevant to the patentability of the presently disclosed subject matter.

BACKGROUND

Endoscopes and imaging catheters are widely used in many medical procedures for viewing areas of body organs, cavities, passageways, etc. Generally, such imaging devices include an elongated sheath or similar structure wherein optical fibers are arranged both for transmitting illumination light to the distal end of the sheath to illuminate a viewing field, and for carrying an optical image back to a viewing port or camera. One or more lenses may be positioned on the distal end of the imaging device to focus the optical image received by the instrument, or the illumination cast by the instrument.

As an aid to the early detection of disease, it has become well established that there are major public health benefits from regular endoscopic examinations of internal structures such as alimentary canals and airways, e.g., the esophagus, lungs, colon, uterus, and other organs. A conventional imaging endoscope used for such procedures comprises a flexible tube with a fiber optic light guide that directs illuminating light from an external light source to the distal tip where it exits the endoscope and illuminates the tissue to be examined. Frequently, additional optical components are incorporated to adjust the spread of light exiting the fiber bundle and the distal tip. An objective lens and fiber optic imaging light guide communicating with a camera at the proximal end of the scope, or an imaging camera chip at the distal tip, produce an image that is displayed to the operator (usually a physician). In addition, most endoscopes include one or more working channels through which medical devices such as biopsy forceps, snares, fulguration probes, and other tools may be passed.

In many applications, it is desirable that the distal portion of the imaging device be "steerable", bendable or maneuverable from the proximal end of the device, to facilitate guidance of the device through tortuous or furcated anatomical passageways. Additionally, the ability to bend the device at or near its distal end may enable the operator to visually scan an expanded viewing area by bending or otherwise manipulating the distal end of the device. The ability to maneuver the tip makes it easier to guide the tip of the device properly through the often highly branched and convoluted passageways near organs.

In order to control deflection of the distal tip of an imaging device, many designs have been introduced that incorporate either two opposed control wires to control bending in one plane, or four wires evenly spaced to control bending in two perpendicular planes. These control wires run the length of the device and terminate at the distal end of the steerable region, or at the distal tip. The proximal end of each control wire is functionally connected to a separate drum or spool rotated manually, or by a dedicated electrical or fluid motor for linearly advancing and retracting the control wire in relation to the device. In operation, when one of the control wires is pulled proximally by rotation of the drum or spool, the distal tip of the device bends at the steerable region toward the retracted wire.

Navigating channels in the human body can be very challenging. Some parts of the human anatomy can be difficult to see and are not always oriented in a convenient location relative to the position of the scope or surgical instrument. Occasionally, the anatomy and the degrees of freedom of the instruments can impede or prevent successful navigation. During conventional colonoscopy procedures, a colonoscope advances through the tortuous sigmoid colon until the colonoscope reaches the descending colon. The colonoscope is manipulated to reduce redundancy in the sigmoid colon. When the sigmoid colon has been straightened, the colonoscope typically further advances through the colon. However, this type of procedure is generally difficult to perform, and/or painful for the patient due to stretching of the colon which occurs upon impact between the colonoscope and the wall of the colon as the colonoscope advances, especially during progression of the colonoscope around the bends of the tortuous sigmoid colon. Navigation of the endoscope through complex and tortuous paths is critical to success of the examination with minimum pain, side effects, risk, or sedation to the patient. To this end, modern endoscopes include means for deflecting the distal tip of the scope to follow the pathway of the structure under examination, with minimum deflection or friction force upon the surrounding tissue. Control cables similar to puppet strings are carried within the endoscope body in order to connect a flexible portion of the distal end to a set of control knobs at the proximal endoscope handle. By manipulating the control knobs, the operator is usually able to steer the endoscope during insertion and direct it to a region of interest, in spite of the limitations of such traditional control systems, which are cumbersome, non-intuitive, and friction-limited. Common problems for operators of traditional endoscopes include their limited flexibility, limited column strength, and limited operator control of stiffness along the scope length.

Conventional endoscopes are generally built of sturdy materials, which decrease the flexibility of the scope and thus decrease patient comfort. Furthermore, conventional endoscopes are complex and fragile instruments that frequently need costly repair as a result of damage during use or during a disinfection procedure. Moreover, many procedures using steerable instruments remain complex. A great deal of skill and patience is often required to correctly orient the instrument in a predetermined position.

GENERAL DESCRIPTION

Intubation is a medical procedure involving the insertion of a tube into the body. For example, in order to scan the colon, the operator needs to insert the endoscope all the way through the colon to the cecum. To perform intubation, the operator typically pushes and rotates the insertion tube with one hand, while controlling the distal tip with his other hand by using control knobs located in the handle of the endoscope. The traditional endoscope has a semi-flexible shaft i.e. it cannot pass through the body lumen in its original shape because it is not flexible enough. Therefore, the operator needs to perform manipulations with the endoscope to reshape the body lumen to an easier path for the endoscope to maneuver. The main way to reshape the body lumen is by rotating the insertion tube. The rotation of the tube first straightens the tube, in order to deliver the torsion forces to the distal tip, affecting the body lumen in the same way. Such manipulations are described in many manuals for training operators, such as, for example, "Colonoscopy: Principles and Practice, Jerome D. Waye, Douglas K. Rex, Christopher B. Williams July 2009, Wiley-Blackwe". However, such manipulations may harm and cause a lot of pain to the patient. To solve this problem, the present invention provides a novel insertion unit being configured and operable to perform intubation of an endoscope by pushing the insertion unit and fully steering and rotating the bending section of an intubation system without straightening the body lumen. In this connection, it should be understood that to minimize pain and risk of perforation associated with the manipulations of the body lumen during intubation, the natural structure of the body lumen should be preserved. The novel configuration of the insertion unit of the present invention enables to insert the insertion unit which maneuvers through the body lumen without exerting large forces on the body lumen, while the operator can deliver enough force of insertion to be able to reach the cecum with the distal tip.

Therefore, according to a broad aspect of the present invention, there is provided an integral insertion unit to be connected to a bending section of a medical instrument. The integral insertion unit comprises an inner elongated shaft structure being capable of torque transmission around its length axis and an outer elongated shaft structure surrounding the inner elongated shaft structure and having a continuous outer surface. The integral insertion unit is configured and operable to transmit pushing and rotation forces along its length, to bend the distal tip in all directions and to fully rotate the distal tip.

The insertion unit may be an integral part of an endoscopic system (e.g. comprising an image capturing device which is steered to any desired destination to enable to image a body lumen and perform polypectomy), or may be coupled to elements forming together an endoscope. The insertion unit refers hereinafter to the part of an endoscope device connecting between a controller being configured to transmit forces from the operator's hand to the bending section of the intubation system and the optical head of the endoscope. The insertion unit of the present invention may be thus connected to any commercially available controller and to any commercially available optical head. As will be described further below, the insertion unit is connected to a bending section via a bending bearing structure. In this connection, it should be noted that each of the insertion unit, the bending section and the bending bearing structure are also independent aspects of the present invention. The insertion unit and/or the bending section and/or the bending bearing structure may be an integral part of an endoscopic system or may be coupled to elements forming together an endoscope. The insertion unit refers hereinafter to the part of an endoscope device connecting between a controller being configured to transmit forces from the operator's hand to the distal tip of the endoscope and a bending section of an endoscope. The insertion unit and/or the bending section and/or the bending bearing structure of the present invention may be thus connected to any commercially available controller and to any commercially available bending section and/or insertion unit and/or bending bearing structure respectively.

Moreover, typically, to perform intubation, the operator typically pushes and rotates the insertion tube with one hand, while controlling the distal tip with his other hand by using control knobs located in the handle of the endoscope. When the medical instrument reaches the region of interest, the operator should hold the medical instrument in the desired position with his hand or by requiring assistance of another person. If the operator withdraws his hand from the medical instrument, the medical instrument may not stay in the desired position, since the body lumen being straightened would move to tend to come back to its natural shape. By using the novel configuration of the present invention, the operator is not required to hold the medical instrument in the desired position. If the operator withdraws his hand from the medical instrument, the medical instrument will stay in the desired position, since the body lumen is not straightened and retains its natural shape.

Moreover, the novel configuration of the insertion unit of the present invention enables to control the distal tip in all directions including both bending the tip to all directions (360°) and fully rotating to both directions. In some embodiments, the integral insertion unit is configured and operable to rotate the distal tip to an extent being higher than 180° clockwise and counter clock wise. The terms "distal tip" and "distal end" are used herein interchangeably and refer to the distal part of the steerable portion of the intubation system being connected to an optical head if the insertion unit is integrated within an endoscope. In this connection, it should be understood that rotation of the distal tip provides full control of the distal tip being necessary for a polypectomy procedure. The distal tip can be rotated to an extent being higher than 180° in two directions without affecting the body lumen structure, and therefore without causing any harm or pain to the patient.

In some embodiments, the insertion unit has three main physical properties: low friction coefficient, high flexibility and high transmission force from the operator's hand to the distal tip.

In some embodiments, the insertion unit comprises an inner elongated shaft and an outer elongated shaft having spring-like properties (e.g. silicon, extruded PEBAX) at least partially surrounding the inner elongated shaft. The inner elongated shaft structure has spring-like and flexibility properties. The shafts are fixed at their distal and proximal ends and therefore cannot be displaced one relative to the other. This configuration provides a good torque transfer mechanism and enables to rotate the scope distal end (bending section and the optic head) without any delay. The optical head rotates together with the bending section.

In some embodiments, the inner elongated shaft structure is configured as an elongated torsion shaft.

In some embodiments, the outer elongated shaft structure is configured as a double layered structure comprising an inner coil hollow spring at least partially covered by a jacket. The jacket may be configured to be stiff enough to prevent closure or kinking and collapse thereof. The jacket may be at least partially coated by a hydrophilic material or is surrounded by a layer being at least partially coated by a hydrophilic material. If the jacket is made of a non-coatable material (e.g. silicon), it is configured to have an additional coatable layer (e.g. thin sleeve) to enable to apply coating on the outer surface of the jacket.

In some embodiments, the inner elongated shaft structure is configured as a double layered structure comprising an inner coil hollow spring at least partially covered by a jacket having a braided outer surface.

In some embodiments, the inner elongated shaft structure and the outer elongated shaft structure are fixed to each other at their distal and proximal extremities via a bearing structure.

In some embodiments, the present invention also provides an insertion unit of a certain flexibility and a variable stiffness/gradually rigidity along its length of such that its flexibility increases in the distal direction. The variable stiffness capability enables to deliver forces along the insertion unit for efficient intubation without affecting the ability to bend in small radiuses. In some embodiments, the present invention also provides stiffening the distal region of the insertion unit. In this connection, it should be noted that this unique configuration enables to stiffen the proximal part of the insertion unit, being close to the orientation controller and facilitates better external control of the position and manipulation of the insertion unit. This may be implemented by placing in the outer elongated shaft structure, a plurality of flexible wires having different lengths to provide different flexibility of the outer elongated shaft structure along its length. The flexible wires are configured to be flexible enough to be capable of being bent, if needed, to fit a body lumen shape. The present invention also provides a novel bending section which may be incorporated or coupled to any endoscopic tool, having better navigation and tracking, a superior interface with the operator, improved access by reduced frictional forces upon the lumenal tissue, increased patient comfort, and greater clinical productivity and patient throughput than those that are currently available. The bending section comprises a flexible channel having a distal end portion; a plurality of spaced-apart elements configured to enable steering of the bending section, the plurality of spaced-apart elements being located in a spaced-apart arrangement along an inner surface of at least the distal end portion of the flexible channel, the plurality of spaced-apart elements being surrounded by the flexible channel; and at least two steering threads having at least a portion passing through the plurality of spaced-apart elements; each of the at least two steering threads being configured to cause the bending of the at least distal end portion of the flexible channel together with the spaced-apart elements thereof, until edges of the spaced-apart elements come into contact, wherein the plurality of spaced-apart elements are fastened along the inner surface of the flexible channel. In the present invention, the bending section may comprise a steering mechanism being formed by spaced-apart steering elements (e.g. rings) placed in the internal volume of a flexible channel. The bending section is configured and operable to bend and rotate the bending section of the medical instrument such that a space is created between the body lumen and an image-capturing device to facilitate imaging of the body lumen and polypectomy. This special configuration, in which the by spaced-apart steering elements are placed on the internal surface of the flexible channel and not on the external surface of the flexible channel protruding outside, enables to reduce the required external space and the forces to be applied to fully steer the bending section, as compared with a bending section above, in which the steering elements are placed above the external surface of the flexible channel. Moreover, the configuration of the novel bending section of the present invention eliminates the need for stiff mechanical linkages between the adjacent links, to ensure bending and rotation, and provides a soft bending section that can be bent and rotated in any possible direction by transmitting bending and torsion forces, thus allowing greater mobility that requires fewer elements.

The flexible channel may be implemented by a non-continuous structure (e.g. a mesh braided structure). The non-continuous structure of the flexible channel enables to transmit torsion forces along the length of the bending section even if the bending section is in a bent position. When a typical tube is bent, it is not capable of transmitting torsion forces along its length. The non-continuous property of the flexible channel enables to transmit rotation forces along the length of the bending section. The braided structure may be at least partially surrounded with a sleeve being or not coated by any hydrophilic material. In this connection, it should be noted that when a structure is inserted into a body lumen, the coating of its external surface by a hydrophilic material provides lubricant properties to the structure.

In some embodiments, the flexible channel is configured to be bent at an angle greater than 180° in every direction.

In some embodiments, the plurality of spaced-apart steering elements are fastened (e.g. rigidly) along the inner surface of the flexible channel. The fastening may be made by any suitable method for example by at least partially applying adhesive material on the steering element by ultrasonic welding or by injection molding.

The bending section is configured such that, in a straight state, when not bent, the spaced-apart elements do not touch each other. When the bending section is in a fully bent state, the spaced-apart elements' edges come into contact.

In some embodiments, the spaced-apart elements are separated by a constant or variable distance between them. The distance between the elements determines the properties of the bending section, such as its flexibility and bending properties, as well as the shape of the bent tip/distal end of the bending section. The distance between the spaced-apart elements may be determined according to the specific material of the bending section. In other words, the spaced-apart elements may be arranged with distances between them selected in accordance with the material of the bending section. The distance between the spaced-apart elements is selected in such a way that it prevents sharp bends of the bending section (i.e. sharp angular pipe fitting) that may lead to narrowing of the channels or the bending section itself, or to a folded portion of the bending section.

In some embodiments, the spaced-apart elements are closed-loop elements (e.g. rings).

In some embodiments, the spaced-apart elements include at least two openings positioned radially at substantially equal angles one from another, such that at least a portion of one thread passes therethrough. The elements are stacked one above the other such that the openings are arranged in a concentric manner. A steering thread is threaded through all concentric holes of all the rings, one thread per each steering direction.

In some embodiments, at least one spaced-apart element has a cross-sectional geometrical shape defining a tapered section from both sides, such that while in a bent state when pulling on at least one steering thread, a U-shape of the bending section is achieved. In this way, the creation of elbows, or folded portions, is prevented. The U-shape of the bending section is determined by the distance between the spaced-apart elements and the angle of the tapered section.

In some embodiments, a portion of the steering threads is positioned within the insertion unit and a remaining portion of the steering threads passes through the spaced-apart elements. Each steering thread is configured to bend the bending section respectively in one steering direction. At least one steering thread has one end fixed to one of an outermost spaced-apart element or the insertion unit's distal end (e.g. flexible channel's distal end), while the other end of the steering thread is free to move. The other end of the steering thread may be connected to a thread pulling device (e.g. a joystick), which, in some embodiments, may be an arrangement of knobs to thereby enable full control of the bending of the bending section at any desired angle. The angle of the bend corresponds to the amount of thread that has been pulled out. Pulling the thread causes a bending momentum in all the rings that it passes through.

In some embodiments, the bending section has three steering threads and the elements have three openings respectively positioned at 120° one from another. In other embodiments, the mechanism has four steering threads and the rings have four openings respectively positioned at 90° one from another. In some embodiments, the end of the steering thread, being free to move, is connected to a knob to thereby enable full control of the bending of the bending section at any desired angle. The connection between the threads and the knob may be made mechanically, electrically, hydraulically, pneumatically or by using any possible connections known in the art.

In some embodiments, the bending section further comprises at least one spring-like sleeve at least partially enclosing at least one of the steering threads, respectively.

According to another broad aspect of the present invention, there is provided an intubation system comprising an insertion unit as described above and an orientation controller, which is attached to the inner elongated shaft, such that when the orientation controller rotates, the bending section turns around itself. The orientation controller is configured and operable to transmit torsion forces from an operator's hand to the distal end, such that rotation of the orientation controller rotates the inner elongated shaft structure inside the outer elongated shaft structure and thereby rotates a distal end of the insertion system around itself, without changing the outer elongated shaft structure's position inside the body lumen. For example, bearings hold the inner elongated shaft and the outer shaft together in their both edges to enable relative rotation. The inner elongated shaft, connected to the orientation controller at one edge and to the bending section at the other, is able to transfer the rotation of the orientation controller directly to the distal tip through the insertion unit, without affecting the position of the insertion unit.

In some embodiments, the intubation system further comprises a first rotation bearing structure connecting between the inner elongated shaft structure and the orientation controller. The bearing structure is configured for allowing the inner elongated shaft to rotate inside the outer elongated shaft of the insertion unit.

In some embodiments, the intubation system further comprises a second bending bearing structure connecting between the outer elongated shaft structure and the bending section and being capable to rotate. The bearing structure is configured for providing, on one hand, a rigid coupling between the bending section and the outer elongated shaft structure, and, on the other hand, a dynamic coupling with the bending section, allowing free rotation of the bending section.

In some embodiments, the second bending bearing structure comprises a first and a second element coupled to each other. The first element is a dynamic element being capable to be connected to the bending section and has the capability of rotating around itself. The second element is a static element capable of being connected to the outer elongated shaft structure, providing a rigid coupling.

In some embodiments, the first element comprises an opening configured to accommodate at least one extremity of a torsion shaft.

In some embodiments, the second bending bearing structure is configured to limit maximum possible angle of rotation of the bending section, and, after the bending section has been rotated at the maximal angle, to have the capability to apply torsion forces on the insertion unit, in order to increase stiffness of a region between the second bearing structure to a point of zero rotation.

In some embodiments, the intubation system further comprises the bending section as described above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In order to better understand the subject matter that is disclosed herein and to exemplify how it may be carried out in practice, embodiments will now be described, by way of non-limiting example only, with reference to the accompanying drawings, in which:

FIGS. 1A-1F illustrate a way an operator, skilled in the art, should manipulate an endoscope for performing endoscopy and/or polypectomy;

DETAILED DESCRIPTION OF EMBODIMENTS

As described above, performing colonoscopy or even polypectomy procedures, requires a lot of skill from the operator to manipulate the distal tip to a desirable position using a therapeutic tool to perform the procedure. Moreover, typically, as illustrated from example in FIG. 1A (http:// www.endoscopy-colon-explorer.com/four-hands-intubation-technique-part-2/) the operator needs to reshape (straighten) the colon by rotating the insertion tube, to be able to advance within the body lumen and properly inspect the tissue. As mentioned above, reshaping is not safe and may cause harm and a lot of pain to the patient. To this end, as illustrated in FIGS. 1B-1F, the operator needs to manipulate the insertion tube and use his entire body in this procedure. In polypectomy processes, the operator needs to navigate the distal tip to examine and remove the polyp. The operator needs to be able to bend the tip in every direction and also rotate the insertion tube in order to get to the right position.

The present invention provides a novel configuration of the insertion unit for performing safe procedures. The insertion unit is configured for guiding an endoscope through a body lumen with low danger to the patient. Navigation of the distal tip is possible by using both deflection of the bending section (e.g. using knobs) and rotation of the bending section and even of the insertion unit, if desired. The novel insertion unit allows the operator to rotate the bending section from the operator's orientation controller, without rotating the insertion unit, if desired. The insertion unit may be also rotated, as will be described further below.

Figure 2A:
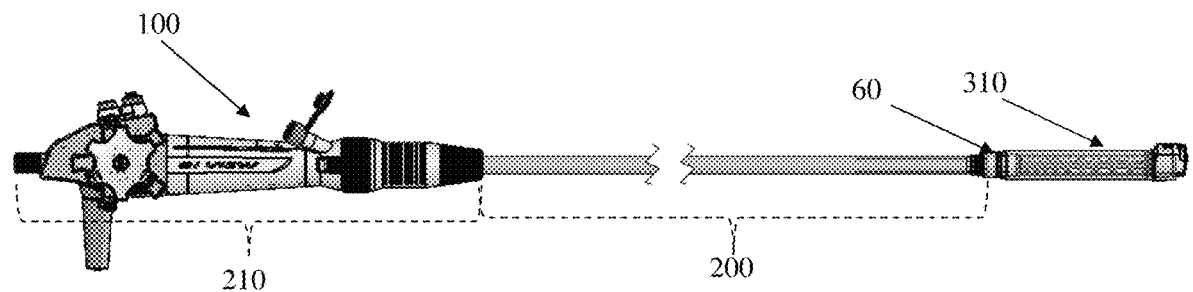
FIG. 2A schematically illustrates an example of an intubation system according to some embodiments of the present invention.

Reference is made to FIG. 2A, illustrating an example of an intubation system 100 incorporating an insertion unit 200 of the present invention. As described above, insertion unit 200 connects between an orientation controller 210 (e.g. a grip comprising valves, steering knobs and electrical buttons) located in the handle, and an optical head. Insertion unit 200 has the capability to advance through a tortuous body lumen fitting the looped configuration of the body lumen shape, transmitting pushing and rotation forces from one extremity to the other, despite the possible looped condition of the shaft. Insertion unit 200 is connected to a bending section 310 via a bending bearing structure 60. Insertion unit 200 is capable of accommodating a plurality of channels running through its length (e.g. for supplying water and/or CO2 and/or air and/or for suction and/or for supplying electricity and/or venting fluid outside the lumen and/or controlling various inflatable device pressures, and/or sensing various inflatable device pressures, and/or sensing body lumen's pressures), as well as steering threads.

Figure 2B:
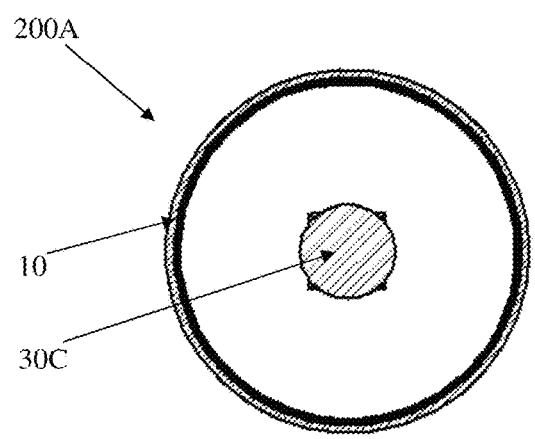
FIG. 2B-2C schematically illustrate possible examples of the insertion unit according to some embodiments of the present invention.

Reference is made to FIG. 2B, illustrating an example of insertion unit 200A comprising an inner elongated shaft structure surrounded by an outer elongated shaft structure 10. Inner elongated shaft structure has thus a diameter smaller than outer elongated shaft structure 10. Moreover, the inner elongated shaft structure and the outer elongated shaft structure 10 form together an integrated/integral insertion unit 200A connecting at its extremities at one side the orientation controller 210 of FIG. 2A and at the other side the bending section 310 of FIG. 2A. As described above, the physical properties required for the insertion unit are appropriate flexibility (a certain flexibility according to the bending radius), follow-up characteristics, a capability to rotate the distal end without rotating the entire insertion unit and restoring performance against bending, pushability and torque transmission performance (generically called "operationality") for transmitting an operational force from the proximal end portion to the distal side, and kink resistance (often called "resistance against sharp bending"). This unique configuration of the inner elongated shaft structure provides good torque transfer, high flexibility and free rotation of the distal tip of the device. As shown in the figure, the inner shaft structure and the outer shaft structure are capable of relative rotation, one with respect to the other.

Inner elongated shaft structure may be implemented by an elongated torsion shaft 30C surrounded by the outer hollow elongated shaft structure 10. In this context, in the specification and in the claims, "torsion shaft" refers to a rotatable flexible non-hollow cable having a non-continuous surface driven by gearing linked to the output of the orientation controller 210 of FIG. 2A. In this connection, it should be understood that, as described above, the insertion unit of the present invention does not straighten the body lumen, and therefore, upon advancing, it will be convoluted around itself according to the body lumen shape. However, when a regular tube is bent and convoluted, it is not capable of transmitting pushing and rotation forces along its length. The non-continuous property of the inner elongated shaft structure enables to transmit pushing and rotation forces along the length of the insertion tube 200A. When the operator turns orientation controller 210, orientation controller 210 turns the torsion shaft 30C. This shaft can transfer a great amount of torsion and remain very flexible. In this connection, it should be understood that since torsion shaft 30C is not hollow, a plurality of channels may be accommodated between the outer structure 10 and the torsion shaft 30C. Moreover, torsion shaft 30C is capable of transmitting torque even if it is wrapped around itself, because of the loops naturally formed by the colon.

Generally, the inner structure is attached at one side to orientation controller 210 of FIG. 2A and to a bending bearing structure 60 of FIG. 2A from the other side. Turning the orientation controller rotates the bending section in turn. As described above, the outer elongated shaft structure prevents buckling/kinking and maintains its round shape, while remaining highly flexible. The inner elongated shaft structure, which does not contact the body lumen, rotates inside of the outer shaft structure, without changing the outer shaft structure's position inside the body lumen, due to its good torque transferability and high flexibility.

Figure 2C:
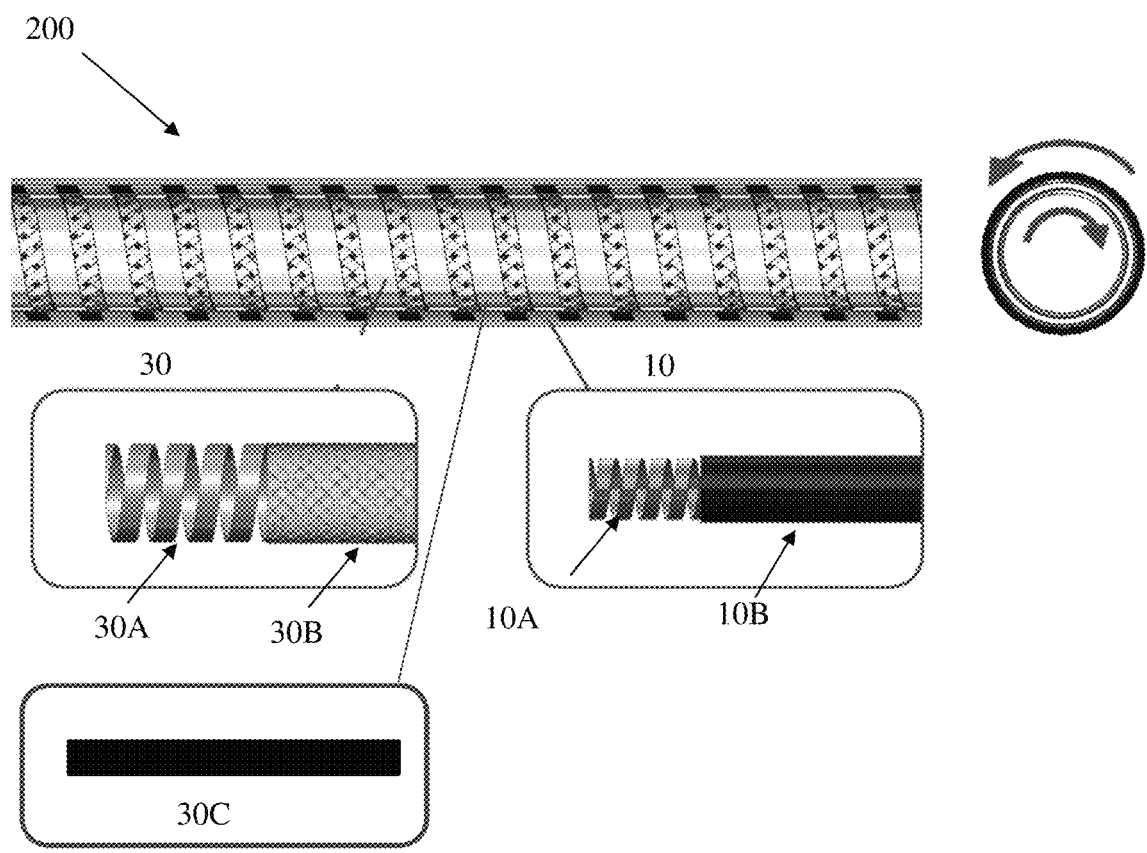

Alternatively, inner structure 30 of the insertion unit 200 may comprise a coil hollow spring covered by a jacket having a non-continuous outer surface forming together a double layered structure. Reference is made to FIG. 2C illustrating the different possible configurations of the inner structure 30 of the insertion unit 200. The non-continuous outer surface may be made of a composite structure and may have a braided/mesh configuration. Inner structure 30 has flexibility properties and is configured and operable to transfer rotation around its length axis. Coil hollow spring 30A is capable of accommodating a plurality of channels running through its length (e.g. for supplying water and/or CO2 and/or for suction and/or for supplying electricity and/or venting fluid outside the lumen and/or controlling various inflatable device pressures, and/or sensing various inflatable device pressures, and/or sensing body lumen's pressures), as well as steering threads. Jacket 30B having a braided outer surface, exhibits a greater effect of preventing kink. In a specific and non-limiting example, coil hollow spring 10A may be a flat wire coil spring and jacket 30B may be a stainless steel wire braid.

Outer elongated shaft structure 10 may be configured as a double layered structure comprising a coil hollow spring 10A covered by a sleeve/jacket 10B having a continuous and optionally flat (e.g. smooth and soft) outer surface. Jacket 10B may be configured as a flexible sleeve being stiff enough to prevent closure or kinking and collapse thereof. The material, the thickness and the structure of the jacket are selected accordingly. In a specific and non-limiting example, jacket 10B is made of a flexible material such as silicon or thermoplastic e.g. PEBAX™. The outer surface of the jacket 10B may be soft and smooth and may be coated by a layer having low-friction properties.

It should be understood that scanning a complicated bent body lumen such as a colon, requires appropriate flexibility and restoring performance against bending, pushability and torque transmission performance (generically called "operationality") for transmitting an operational force from the proximal end portion to the distal side, and kink resistance (often called "resistance against sharp bending"). In this context, in the specification and in the claims, "proximal" means closer to the orifice—mouth or rectum—through which the insertion unit is originally inserted, and "distal" means further from this orifice. Therefore, the insertion unit is configured to have the above-mentioned properties. More specifically, the pushability means the characteristics of the insertion unit that can reliably transmit a pushing force given by an operator at the base end of the insertion unit to the distal end thereof. The torque transmission ability means the characteristics that can reliably transmit rotational force applied to the base end of the insertion unit to the distal end thereof. Further, it is also required for an insertion unit to have follow-up characteristics and kink resistance characteristics. The follow-up characteristics mean the ability by which the insertion unit can advance smoothly within a meandered body lumen without causing injury to the body lumen walls. Moreover, in order to effectively exhibit these characteristics, the outer surface of the jacket 10B may possess lubrication characteristics.

In some embodiments, jacket 10B is at least partially coated by using a hydrophilic coating minimizing the friction forces of the insertion and improving the sliding performance of the insertion unit in the body lumen, thereby further enhancing operationality of the device the insertion unit is mounted on. In a specific and non-limiting example, coil hollow spring 10A may be a flat wire coil spring and jacket 10B may be made of a block copolymer such a soft thermoplastic elongated shaft (e.g. extruded/over extrusion PEBAX™), polyurethane (TPU), silicon or other material. In this connection, it should be noted that if the jacket is made for example of silicon, a coating cannot be applied on its external surface. In this case, a very thin sleeve made of another coatable material should be added over the jacket 10B to coat its external surface.

Figure 2D:
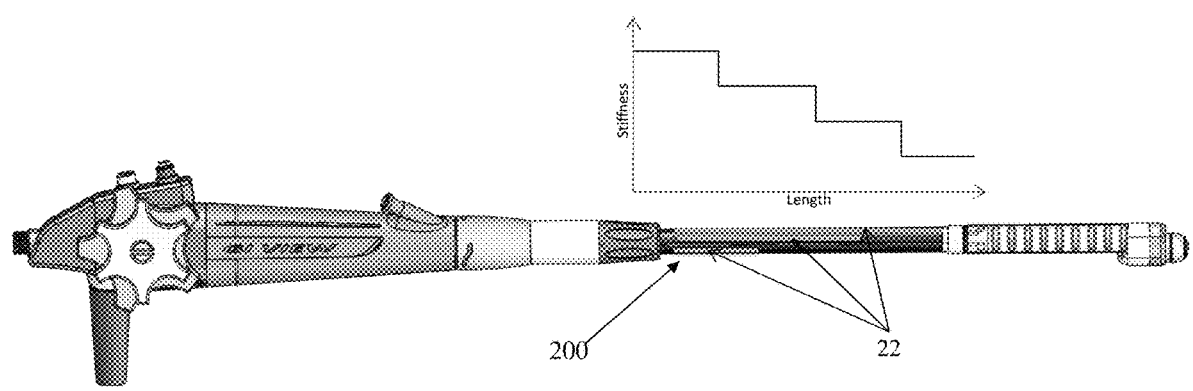
FIG. 2D schematically illustrates an example of an intubation system having a variable stiffness according to some embodiments of the present invention.

Reference is made to FIG. 2D, illustrating an example of a medical instrument in which the insertion unit of the present invention is incorporated. In this embodiment, the insertion unit 200 has a variable/gradual stiffness (e.g. varying elasticity) along its length, such that transmission forces applied to the proximal end increase in the distal direction. This may be implemented by adding at least one flexible wire 22 (e.g. stainless steel) along the insertion unit length (e.g. through/beside inner elongated shaft structure 30). The wires are configured to be flexible enough to be capable to be bent if needed to fit the body lumen shape. The wires are made of shape memory material such as spring steel. For example, in some embodiments, a plurality of wires 22 having different lengths are incorporated into the insertion unit such that the elongated shaft structure's stiffness is divided in a plurality of sections corresponding to the plurality of wires 22 having different lengths.

In this context, the variable/gradual stiffness of the elongated shaft structure along its length refers to the capability of the insertion unit to keep the same bending radius without buckling, while increasing force applied to the insertion unit.

For example, the ratio between the bending radiuses to the insertion unit radius is selected to be very low due to the structure of the insertion unit and its flexibility. More specifically, the ratio K between the bending radius and the insertion unit radius is defined as: $K=R/r$ where R is the bending radius the r is the insertion unit radius.

In a specific and non-limiting example, $K=38.00/6.65$; $K=5.7$

As described above, the pushability and torque transmission performance defines the force delivery capability of the device between the operator's hand and the distal tip of the device. The force delivery capability of the device is a function of the depth of insertion into the body lumen of the insertion unit and of the friction applied on the insertion unit. When the insertion unit advances within the lumen, the variable stiffness of the elongated shaft structure increases linearly together with the friction applied on the structure and the depth of the insertion unit in the body lumen and therefore with the pushing forces.

Figure 3A:
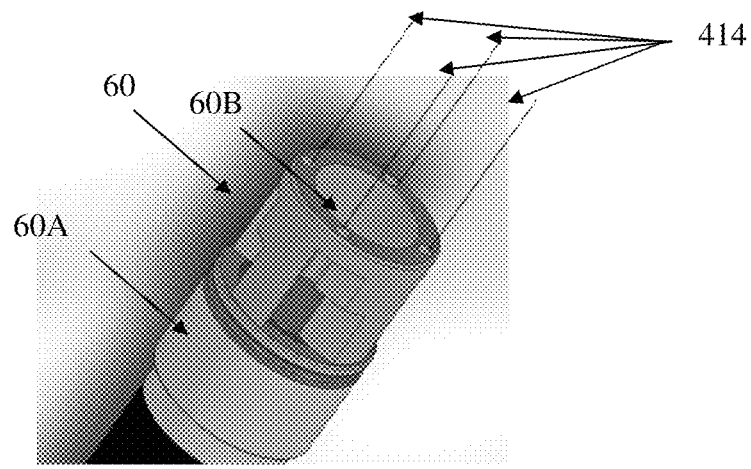
FIGS. 3A-3C schematically illustrate partial views of possible configurations of a bending bearing structure, according to some embodiments of the present invention.

Reference is made to FIG. 3A illustrating an example of the configuration of a bending bearing structure 60 to be connected to the outer elongated shaft structure at one side (e.g. by pressure or by adhesive) and to the bending section of the intubation system at the other side, according to some embodiments of the present invention. Bending bearing structure 60 is configured and operable to provide a rigid coupling between the bending section and the outer elongated shaft structure. This allows the capability to bend the bending portion at minimal force without straightening the body lumen, due to the unique torque transfer capabilities of the insertion unit while not affecting the outer surface of the shaft. In this connection, it should be noted that conventional commercially available colonoscopes are not capable of transferring torque if the shaft is enwrapped around itself three times, and therefore are not capable of fully steering the distal tip.

The bending bearing structure 60 is capable to rotate, to thereby allow free rotation of the bending section. To this end, bending bearing structure 60 may be formed by first and second elements 60A and 60B coupled to each other. The first element 60A is static and is configured and operable to be connected to the outer elongated shaft structure. The second element 60B is configured and operable to be connected to the bending section (e.g. to a steering ring or to the flexible channel) and has the capability of rotating around itself, being thus a dynamic element.

For example, bending bearing structure 60 holds the extremities of spring-like sleeves at least partially enclosing each steering thread as will be described further below with respect to of FIGS. 5B-5C. In this configuration, the steering spring-like sleeves (not shown) may be accommodated within the coil spring 30A of an inner elongated shaft structure 30 of FIG. 2C and are attached at one extremity to the bending bearing structure 60 (e.g. with adhesive). Bending bearing structure 60 comprises a plurality of openings through which the steering threads can pass towards the bending section.

Figure 3B:
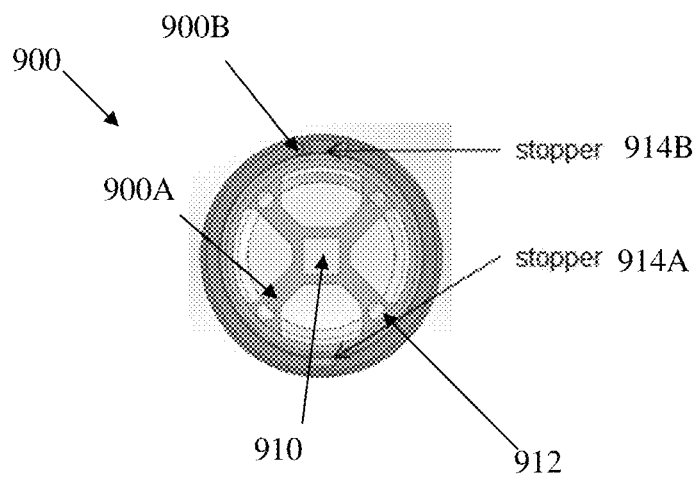

As described above, in some embodiments, the inner elongated shaft structure may be implemented by an elongated torsion shaft surrounded by the outer hollow elongated shaft structure. Reference is made to FIG. 3B illustrating an example of the configuration of a bending bearing structure 900 to be connected to the torsion shaft at one side (e.g. by pressure or by adhesive) and to the bending section of the intubation system at the other side, according to some embodiments of the present invention. As in the previous example, bending bearing structure 900 is capable to rotate around itself in two directions (clockwise or counterclockwise) to thereby allow free rotation of the bending section. To this end, bending bearing structure 900 may be formed by first and second elements 900A and 900B (e.g. rings) coupled to each other. The first element 900A is dynamic and is configured and operable to be connected to the torsion shaft and to the bending section and has the capability of rotating around itself. The second element 900B is configured and operable to be connected to the outer elongated shaft structure.

In this specific and non-limiting example, dynamic element 900A comprises an opening 910 configured an operable to hold an extremity of the torsion shaft. Dynamic element 900A may comprise a plurality of openings 912 configured for accommodating the spring-like sleeves through which the steering threads can pass towards the bending section.

It should be noted that the rotation of the bending section is performed by using this configuration via the torsion shaft. If the angle of rotation is limited, the bending bearing structure 900 would turn around itself and would transfer the rotation forces, first to the bending section and thereafter to the insertion unit because of the dynamic coupling of the bending bearing structure between the elongated shaft structure and the bending section. However, as described above, the insertion unit may accommodate multiple channels, which might buckle, hindering operation of the medical instrument. The bending bearing structure 900 is configured to limit the maximum possible angle of rotation of the bending section. In a specific and non-limiting example, the maximum possible angle of rotation of the bending section may be around 340° (about 170° in each direction). Moreover, in some embodiments, the bending section and the bending bearing structure may be covered together by a sealed sleeve preventing liquid infiltration within the insertion unit. The sleeve allows the bending bearing structure to rotate freely until the sleeve starts to stretch around the bending section, and applies large forces against the rotation. To this end, the bending bearing structure 900 comprises two stoppers 914 positioned in diametrically opposite positions being configured and operable to limit the angle of rotation of the bending bearing structure 900. If rotation of the bending bearing structure were not limited, the resistance forces exerted by the sleeve would stop the rotation and could deteriorate the outer surface of the sleeve, possibly leading to a sealing break. However, a wider range of rotation (above 340°) is necessary to allow the operator to inspect every part of the body lumen while trying to perform a polypectomy procedure.

Figure 3C:
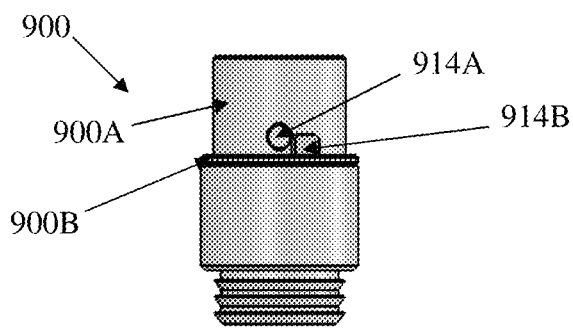

In this connection, it should be understood that, typically, the operator would prefer to rotate the device until the polyp is shown in a 6 o'clock direction to the tool exit point. If the polyp is found at the 12 o'clock direction, by using commercially available devices, the operator needs to rotate the tool by 180° to bring the polyp to the desirable location. To this end, the operator manipulates the device back and forth, to try to keep the desired position, while rotating the tool. This procedure is unsafe and not accurate, losing the precise location of the polyp and consuming time. The novel configuration of the proposed insertion unit solves the above-mentioned problem. In this connection, reference is made to FIG. 3C illustrating another view of the example of the bending bearing structure 900 of FIG. 3B above. Bending bearing 900 is formed by a first and second elements 900A and 900B (e.g. rings) coupled to each other. The first element 900A is dynamic and is configured and operable to be connected to the torsion shaft and to the bending section, and has the capability of rotating around itself. The second element 900B is configured and operable to be connected to the outer elongated shaft structure. First element 900A comprises a stopper 914A and second element 900B comprises a stopper 914B being configured and operable to limit the angle of rotation of the bending bearing structure 900. The first element 900A is also able to rotate around itself, until stopper 914A blocks stopper 914B. As illustrated, after the operator reaches full free rotation of the bending bearing structure, stoppers 914B block rotation of the first element 900A, locking the bending bearing structure at an angle of about 170° in each direction. The operator can continue applying force in the same direction, and the torsion forces applied on the bending bearing structure, rotates first and second element 900A and 900B together (stopper 914A pushes stopper 914B) and starts rotating the outer elongated shaft structure in the same direction. Full rotation of the bending section will rely only on the ability of the torsion shaft (or inner coil) to apply force on the bending bearing structure which rotates the far edge of the outer elongated shaft structure. This unique configuration enables to rotate the distal tip of the bending section around itself by applying external rotational forces on the orientation controller.

As described above, when the bending section is rotated, there is a risk of damaging the inner channels containing fluids. The insertion unit of the present invention enables keeping the channels safe from damage because the rotation angle is very small. The torsion shaft rotates the bending bearing structure and starts rotating the channels around it until the point of zero rotation. This creates a torsion angle for a relatively long distance, minimizing the risk of tubing damages or kinks.

This unique configuration of the insertion unit of the present invention enables to provide together with steering capabilities, rotating capabilities leading to an accurate, rapid and safe procedure enabling to target and to treat any precise location of the polyp. As mentioned above, this unique configuration provides the capability to convey the polypectomy tool at any three-dimensional desired location and position. In some embodiments, the bending section comprises spaced-apart steering rings fixed on the internal space of an external mesh braided sleeve structure. Rotation of the bending section at the same angle as the bending bearing structure is possible due to the braided sleeve structure of the bending section. The bending section structure is capable of transferring large torsion forces while bending due to the unique structure of the braided sleeve having a mesh flexibility structure. The braided sleeve structure can be made from different types of material (plastics, metals), and have a different types of structure (angle, wires).

This unique configuration provides, to the bending section, the capability to bend at an angle exceeding 180° in every direction. This angle can be achieved due to the flexibility of the bending section, the low forces required to be applied to reach this angle, and the structure of the bending section. The flexibility of the bending section is due to the structure of the bending section of the present invention. In particular, the steering rings and the braided structure allow maximum movement without locking. The bending section allows the operator to rotate the orientation controller and reach maximum angle without locking the mechanism. Due to the structure and the flexibility of the bending section (i.e. flexible tubes accommodated inside the bending section), the materials of the bending section's elements and the thin layer on top of the braided sleeve, the forces required to reach maximum angle and a very small bending radius (inner radius of about 10 mm and outer radius being equal to about the inner radius and the diameter of the steering elements as will be described below e.g. 24 mm) are very low as compared to other conventional colonoscopes commercially available.

Figure 4A:
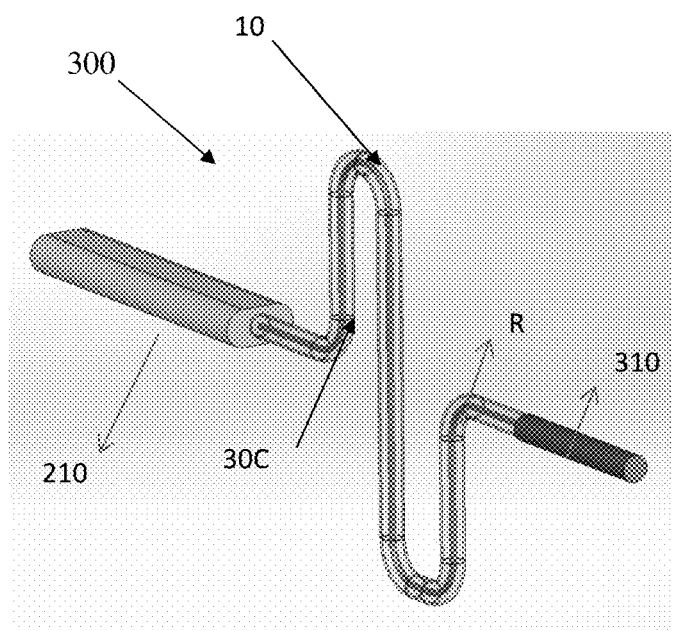
FIG. 4A schematically illustrates an example of an endoscopic device having several bent regions and a zero rotation point according to some embodiments of the present invention.

Reference is made to FIG. 4A illustrating a configuration of the intubation system 300, in which the elongated shaft structure has several bent regions fitting the natural shape of the body lumen. As described above, rotation of the torsion shaft causes, firstly, the bending section 310 to rotate together with the optical head. Because the outer elongated shaft 10 is not connected to the dynamic element of the bending bearing (900A of FIG. 3B) and is continuous and relatively stiff, the structure of the outer elongated shaft 10 does not have torque transmission capabilities, and therefore does not rotate through the length of the shaft 10, in particular when it is in a wrapped condition. After the bending section has been rotated at the maximal angle as described above, if the operator decides to continue to apply rotation forces on the insertion unit, the outer shaft 10 rotates by the movement of stopper 914A of the dynamic element 900A of FIG. 3B that pushes the stopper 914B of the static element 900B in the bending bearing structure (60 of FIG. 3A) that connected to the outer elongated shaft. The insertion unit can be easily rotated until the point of zero rotation R which is the last bending point of the outer shaft (or the connection between the orientation controller and the outer shaft if the outer shaft is straight). After point of zero rotation R, the proximal portion of the outer shaft 10 does not rotate around itself.

Figure 4B:
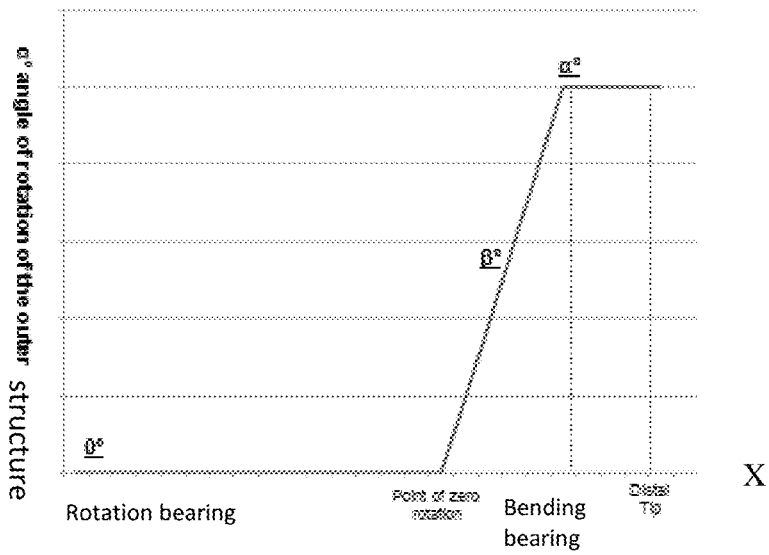
FIG. 4B shows a graph representing the angle of rotation of the outer elongated shaft structure in each section as a function of the length X between the orientation controller and the cutting section of the tube using the insertion unit of the present invention.
Figure 4C:
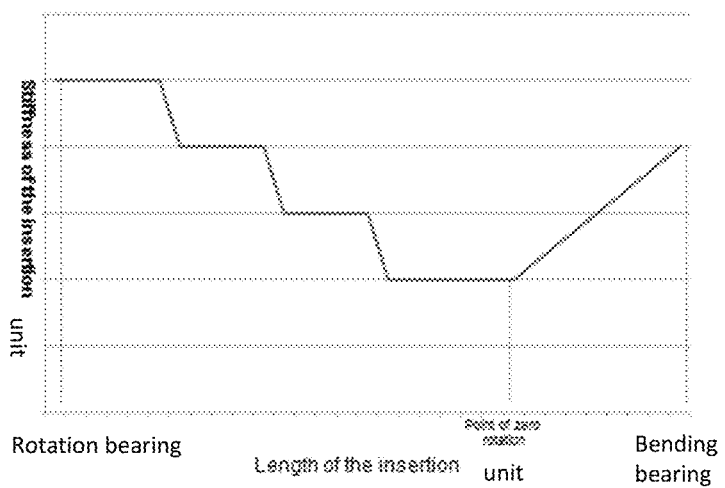
FIG. 4C shows a graph representing the stiffness of the insertion unit as a function of the length of the insertion unit according to some embodiments of the present invention.

Reference is made to FIG. 4B illustrating the angle of rotation of the outer shaft in each section as a function of the length X between the orientation controller and the bending section, using the insertion unit of the present invention. FIG. 4C illustrates the stiffness of the insertion unit as a function of the length of the insertion unit. It is shown in the figure, that in case that the operator applies torsion forces on the insertion unit, after the bending section has been rotated at the maximal angle, the stiffness of the region between the bearing structure to the point of zero rotation increases.

Figure 5A:
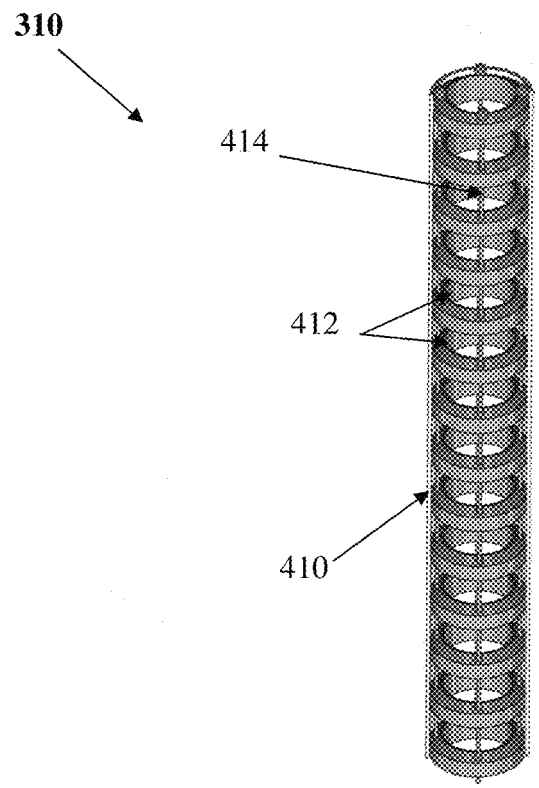
FIGS. 5A-5D schematically illustrate partial views of an example of a bending section according to some embodiments of the present invention.
Figure 5B:
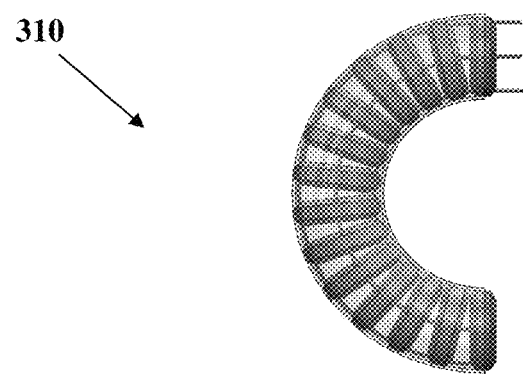

Reference is made to FIGS. 5A-5B exemplifying one possible configuration of the bending section 310 of the present invention comprising elements 412 having a closed-loop configuration surrounded by a flexible channel 410 and configured to be threaded by the steering threads 414 forming. The bending section refers hereinafter to the section of the intubation system in which closed-loop elements are accommodated. This section enables deflection of the distal tip in four main directions. Deflection of the distal tip is necessary to ease intubation, scanning and removal of polyps. The bending section 310 may be an integral part of an endoscopic system.

Although the elements 412 are represented as having a ring-like shape configuration, any shape matching the external shape of the insertion unit may also be used.

FIG. 5A exemplifies the straight state (non-bent) in which the rings do not touch each other. The combination of the flexible channel 410 and spaced-apart elements 412 provides a steerable bending section having bending and torsion properties even in a bent state. The bending and torsion properties are obtained due to the special configuration of the bending section of the present invention comprising spaced-apart elements not linked by a mechanical connection. The material used for this portion has the following physical properties: low bending forces (shear and normal stress), rotating capabilities, and small bending radius. For example, such material may be a braided sleeve made from PET, Nylon, Mylar, Vinyl, Polyolefin, PVDF, Polyethylene, Silica, Aramid, PEEK, PPS, PFA, ECTFE, Copper, Stainless Steel, Brass or a blocked sleeve made from any elastomer or polymer.

The flexible channel 410 may be a flexible sleeve on which the spaced-apart elements 412 are provided along its length for increased stiffness and to help prevent kink and collapse of the sleeve. In some embodiments, the external surface of the flexible channel may be smooth, flat (without protrusion) facilitating navigation and insertion into a body lumen, and also contributing to the ease of applying low friction coatings (hydrophilic/hydrophobic), when needed. The flexible channel 410 is configured as a jacket which may have at least one of the following configurations: a thin-walled tubular member, and a braided sleeve. Therefore, in some embodiments, the bending section of the present invention is capable of full steering, as well as full rotation around itself, providing accurate imaging and polypectomy.

In some embodiments, the bending section can be manipulated by at least two pulling threads, enabling full control of the steering of the bending section at any desired angle. In a specific and non-limiting example, steering of the optical head is implemented by pulling and releasing at least two steering threads 414 attached to the optical head at one side of the device, and at one pulley at the other. Each steering thread 414 bends the bending section in one steering direction. Each steering thread 414 is configured to transfer a pulling force to the distal end of the bending section in order to bend it. One end of each steering thread 414 is rigidly fixed to the flexible channel (shown as S in FIG. 5D below) or to the outermost spaced-apart element while the other end of the steering thread 414 is free to move (shown as S' in FIG. 5D below). The steering threads 414 are configured and operable to steer the bending portion 310 in which the spaced apart elements 412 are incorporated, by pulling at least one end of at least one steering thread 414.

Moreover, the steering threads 414 and the spaced-apart elements 412 are located inside of the flexible channel 410, which protects them from environment factors (such as moisture, heat, acids, etc.). Furthermore, for spaced-apart elements having the same dimension, this novel configuration in which the plurality of spaced-apart elements are surrounded by the flexible channel, leaves more space in the volume defined by the inner surface of the spaced-apart element than when the spaced-apart elements are positioned over the flexible channel. In this connection, it should be noted that the space/volume available within the channel is an important parameter of the system, since, typically, a bending section is associated with a plurality of tubes passing therethrough. As described above, the plurality of tubes passing therethrough may be configured for at least one of supplying water, supplying electricity, venting fluid outside the lumen, and controlling various inflatable device ("balloon") pressures, sensing various inflatable device ("balloon") pressures, and sensing body lumen's pressures (e.g., sensing pressure distal to apparatus).

In some embodiments, the spaced-apart elements 412 may be fastened to the inner surface of the flexible channel by adhesion. The spaced-apart elements 412 may be rigidly fastened along the flexible channel 410. Fastening of the elements on the flexible channel may be carried out by any suitable method, for example by at least partially applying adhesive material on the steering element by ultrasonic welding or by injection molding. The spaced-apart elements 412 may be maintained by the flexible channel or rigidly fastened along the channel. The spaced-apart elements 412 may be separated by a variable or constant distance between them. The distance between the elements determines the properties of the bending section such as its flexibility and bending properties as well as the shape of the bent tip. The distance between the spaced-apart elements is determined according to the specific material of the flexible channel.

FIG. 5B exemplifies a fully bent state in which the ring's edges come into contact. Pulling a steering thread 414 causes bending momentum in all the rings that it passes through. In this configuration, the steering threads 414 are thus also surrounded by the flexible channel protecting them from interaction with the surroundings. This ability of protecting the steering threads and the spaced-apart elements from contact with the body lumen, enables to use a large range of materials for manufacturing the steering threads and the spaced-apart elements which do not have to be in compliance with requirements for materials being inserted into a body lumen.

As described above, the appropriate selection of distance between the steering elements enables an optimal steering in any direction, and at any angle. The amount of the spaced-apart elements 412 may be variable and depends on the required maximal bending radius, channel flexibility and the width of each spaced-apart element.

The bending section provides the steering capability of being displaced to any steering direction, and being bent to any angle. The bending of the bending section is provided by compressing one side (the bending side) and stretching the other (outer to the bend).

Figure 5C:
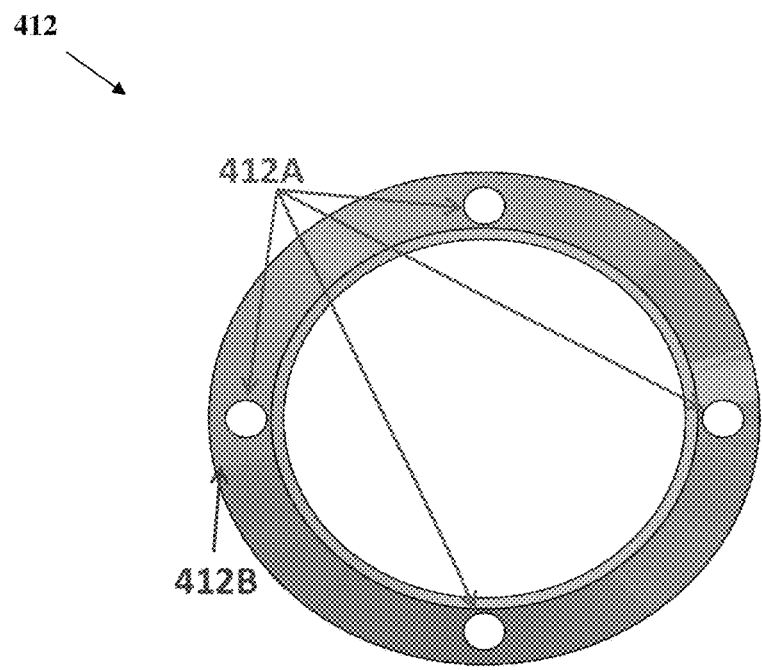

Reference is made to FIG. 5C exemplifying a cross-sectional view of the ring-like element 412. As exemplified in FIGS. 5A-5B, in some embodiments, the ring-like element is configured such that its cross-sectional shape defines a tapered section from both sides to ensure that while in a bent state when pulling on the steering threads, a U-shape of the channel would be achieved to prevent the creation of elbows or folded portions. In this specific and non-limiting example, the ring-like element has four openings 412A positioned radially at equal angles one from another (at 90°) through which at least a portion of the steering threads is intended to pass. However, the invention is not limited to such a configuration and the number of openings may be two or three. Generally, each ring contains at least two openings positioned radially at equal angles, one from another. The rings are stacked, one above the other, such that the openings are arranged in a concentric manner. A steering thread is threaded through all concentric holes of all the rings, one thread per each steering direction. The outer surface 412B of the ring-like element is surrounded by the flexible channel. As described above, the ring-like element may be enclosed by the flexible channel or may be fastened to the inner surface of the flexible channel. The flexible channel is thus configured as a sleeve enclosing the plurality of spaced-apart elements and protecting them from contact with the surroundings. Contact of the bending section with the body lumen is thus made via the external surface of the flexible channel, being a flat surface without indentation or protrusion, which facilitates insertion and navigation of the device/tool on which it is mounted. The flexible channel may be then coated by a hydrophilic solution for reducing friction forces during advancement of the device. In case of a braided sleeve, it might be covered by a very thin sleeve and the coating will be applied on it.

Figure 5D:
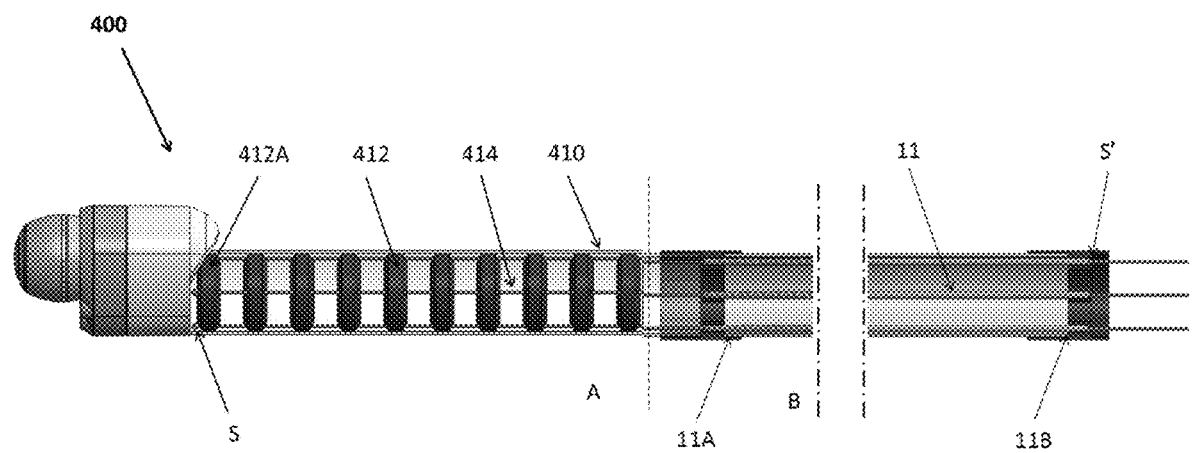

Reference is made to FIG. 5D exemplifying a partial view of a bending section 400 according to some embodiments of the present invention. In some embodiments, each steering thread 414 may be at least partially enclosed by a spring-like sleeve 11 respectively. The extremities of the sleeves are fixed to the non-steerable portion B of the guiding tube 10 at two points 11A and 11B. As described above, one end of each steering thread 414 is rigidly fixed to the flexible channel (shown as S) or to the outermost spaced-apart element, while the other end of the steering thread 414 is free to move (shown as S'). As described above, the bending bearing structure 60 of FIG. 3A may hold the extremities of spring-like sleeves at least partially enclosing each steering thread. The portion of the steering threads 414 passing through the spaced-apart elements 412 may not be enclosed by the sleeves 11 while the remaining portion may be enclosed by the sleeves 11. The sleeves 11 may be flexible closed coil spirals having an incompressible part that allow sliding movement of steering threads inside. The steering threads 414 at least partially enclosed by the spring-like sleeves 11 may be configured as a Bowden cable. It should be noted that, as is well known in the art, a Bowden cable is a type of flexible cable used to transmit mechanical force or energy by the movement of an inner cable (most commonly of steel or stainless steel) relative to a hollow outer cable housing. In the present invention, the inner cable is the steering thread and the housing is the spring-like sleeves. The housing is generally of composite construction, consisting of a helical steel wire, often lined with nylon, and with a plastic outer sheath. The linear movement of the inner cable is most often used to transmit a pulling force. Therefore, the spring-like sleeve 11 may be made of a close-wound helix of round or square steel wire.

The invention claimed is:

1. An integral insertion unit to be connected to a bending section of a medical instrument to be inserted into a body cavity; said integral insertion unit comprising:
   an inner elongated shaft structure being configured for torque transmission around its length axis; and
   an outer elongated shaft structure surrounding concentrically said inner elongated shaft structure; the outer elongated shaft structure having a continuous outer surface;
   a bending bearing structure connectable to a distal end of said outer elongated shaft structure at one side and to the bending section at the other side, wherein said bending bearing structure comprises a first and second elements coupled to each other;
   the first element being connected to the inner elongated shaft structure and the second element being connected to the outer elongated shaft structure; wherein
   the first elements comprises an opening through which the inner elongated shaft structure is connected to the bearing structure, and the second element comprises an opening through which the outer elongated shaft structure is connected to the bearing structure, each opening of the first and second elements being configured to accommodate a respective extremity of the inner elongated shaft structure and of the outer elongated shaft structure;
   said first element is a dynamic element being capable to be connected to the bending section and having the capability of rotating around itself;
   said second element is a static element providing a rigid coupling between the bending section and the outer elongated shaft structure;
   said bearing structure being configured for allowing the inner elongated shaft to rotate inside the outer elongated shaft;
   wherein said dynamic element comprises a first stopper and the static element comprises a second stopper, said first stopper being configured to block second stopper when further rotation of the bending bearing structure blocks the rotation of said dynamic element and of the inner elongated shaft structure, to thereby enable locking the bending bearing structure, rotating said dynamic and static elements together and further rotating the outer elongated shaft; wherein said integral insertion unit is configured and operable to transmit pushing and rotation forces along its length, to bend a distal tip in all directions and to fully rotate the distal tip.

2. The integral insertion unit of claim 1, wherein said inner elongated shaft structure comprises at least one of an elongated torsion shaft or a double layered structure comprising an inner coil hollow spring at least partially covered by a jacket having a braided outer surface.

3. The integral insertion unit of claim 1, wherein said outer elongated shaft structure comprises a double layered structure comprising an inner coil hollow spring at least partially covered by a jacket.

4. The integral insertion unit of claim 1, wherein said outer elongated shaft structure accommodates a plurality of flexible wires having different lengths, wherein each flexible wire is configured to be flexible enough to be configured for being bent, if needed, to fit a body lumen shape.

5. The integral insertion unit of claim 1, wherein said inner elongated shaft structure and said outer elongated shaft structure are fixed to each other at their distal extremities via said bending bearing structure being configured for holding both extremities of the inner elongated shaft structure and the outer elongated shaft structure together.

6. The insertion unit of claim 1, wherein said bending bearing structure is capable of rotating and is configured for providing a dynamic coupling with the bending section, allowing free rotation of the bending section.

7. The integral insertion unit of claim 1, wherein said bending bearing structure is configured to limit maximum possible angle of rotation of the bending section, and, when rotation forces are applied on the insertion unit, the outer elongated shaft structure rotates by the movement of the first stopper that pushes the second stopper until a point of zero rotation, wherein the point of zero rotation defines a last bending point of the outer elongated shaft structure.

8. An intubation system comprising: an integral insertion unit of claim 1; and
an orientation controller being attached to the inner elongated shaft structure and being configured and operable to transmit torsion forces from an operator's hand to said distal end;
such that rotation of the orientation controller rotates said inner elongated shaft structure inside said outer elongated shaft structure and thereby rotates a distal end of the integral insertion unit around itself without changing the outer elongated shaft structure's position inside the body lumen.

9. The intubation system of claim 8, further comprising a first rotation bearing structure connecting between the inner elongated shaft structure and the orientation controller, said first rotation bearing structure being configured for allowing the inner elongated shaft to rotate inside the outer elongated shaft of the insertion unit.

10. The intubation system of claim 8, further comprising the bending section comprising a flexible channel having a distal end portion; a plurality of spaced-apart elements configured to enable steering of the bending section, said plurality of spaced-apart elements being located in a spaced-apart arrangement along an inner surface of at least the distal end portion of the flexible channel, said plurality of spaced-apart elements being surrounded by said flexible channel; and at least two steering threads having at least a portion passing through said plurality of spaced-apart elements; each of the at least two steering threads being configured to cause the bending of said at least distal end portion of the flexible channel together with the spaced-apart elements thereof, until edges of the spaced-apart elements come into contact.

* * * * *